United States Patent [19]

Fertig

[11] Patent Number: 4,903,248
[45] Date of Patent: Feb. 20, 1990

[54] PHOTO-ACOUSTIC DETECTOR

[75] Inventor: Glenn H. Fertig, Natrona Heights, Pa.

[73] Assignee: Mine Safety Appliances Company, Pittsburgh, Pa.

[21] Appl. No.: 256,974

[22] Filed: Oct. 13, 1988

Related U.S. Application Data

[62] Division of Ser. No. 165,750, Mar. 9, 1988, Pat. No. 4,866,681.

[51] Int. Cl.$^4$ .................................. H04R 23/00
[52] U.S. Cl. .................................. 367/140; 250/341; 250/336.1; 356/432; 356/216
[58] Field of Search .................. 250/352, 341, 336.1, 250/345; 356/432, 216; 73/606; 367/140, 141

[56] References Cited

U.S. PATENT DOCUMENTS

| | | | |
|---|---|---|---|
| 3,948,345 | 4/1976 | Rosencwaig | 73/659 |
| 4,184,768 | 1/1980 | Murphy et al. | 356/216 |
| 4,299,494 | 11/1981 | Badoz et al. | 374/17 |
| 4,408,478 | 10/1983 | Bechthold et al. | 73/24 |
| 4,543,486 | 9/1985 | Rose | 219/121.14 |
| 4,666,308 | 5/1987 | Williams | 350/358 |
| 4,683,750 | 8/1987 | Kino et al. | 73/606 |

Primary Examiner—Deborah L. Kyle
Assistant Examiner—J. Woodrow Eldred
Attorney, Agent, or Firm—Reed, Smith, Shaw & McClay

[57] ABSTRACT

The present invention pertains to a photo-acoustic apparatus for detecting energy that exits from the end of an optical fiber waveguide device. The photo-acoustic apparatus includes a housing having an opening through which the end of the optical waveguide device extends into the housing. The gas fills the housing and is capable of absorbing energy that exits the end of the optical waveguide device. The gas increases in pressure corresponding to the energy absorbed by it. There is also a pressure sensor such as a capacitor microphone disposed in said housing which is capable of sensing the pressure of the gas and producing an electrical signal proportional to the energy which exits the optical waveguide device. Alternatively, a solid absorber is disposed in the housing that absorbs energy that exits from the end of the optical waveguide device. The gas filling the housing, in this case, does not absorb any of the energy.

3 Claims, 1 Drawing Sheet

PHOTO-ACOUSTIC DETECTOR

This is a divisional of co-pending application Ser. No. 07/165,750, now U.S. Pat. No. 4,866,681, filed on Mar. 9, 1988.

FIELD OF THE INVENTION

The present invention is related to a photo-acoustic detector. More specifically, the present invention is related to a photo-acoustic detector that has a capacitor microphone which senses the pressure of a gas. The pressure of the gas corresponds to the energy which exits an optical waveguide device.

BACKGROUND OF THE INVENTION

The use of optical waveguides, and specifically optical fibers, has become common in sensors of all types. One important aspect of these sensors is accurately detecting the energy that exits from the optical waveguide. Several methods have been devised to detect this energy. See Paul A. Willis; Industrial Research and Development, September, 1982.

These methods of detection all have difficulties in efficient energy conversion. Light energy to electrical energy conversion is inefficient because the modes of the radiation energy exiting from the end of the optical waveguide at large angles do not permit efficient energy coupling to these photodetectors.

SUMMARY OF THE INVENTION

The present invention pertains to a photo-acoustic apparatus for detecting energy that exits from the end of an optical fiber waveguide device. The photo-acoustic apparatus is comprised of a housing having an opening through which the end of the optical waveguide device extends into the housing. A gas fills the housing and is capable of absorbing energy that exits the end of the optical waveguide device. The gas increases in pressure corresponding to the energy absorbed by it. There is also a pressure sensor disposed in the housing which is capable of sensing the pressure of the gas and producing an electrical signal proportional to the energy which exits the optical waveguide device. Alternatively, a solid absorber is disposed in the housing that absorbs energy that exits from the end of the optical waveguide device. The gas filling the housing, in this case, does not absorb any of the energy.

BRIEF DESCRIPTION OF THE PREFERRED EMBODIMENT

Figure 1:
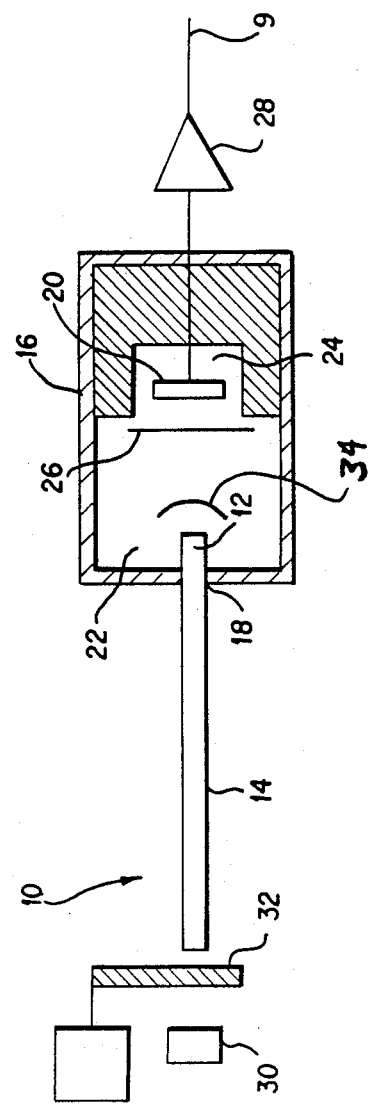
FIG. 1 is a schematic representation of the photo-acoustic apparatus.

There is shown a photo-acoustic apparatus 10. The photo-acoustic apparatus 10 detects energy that exits from the end 12 of an optical waveguide device 14 such as an optical fiber or an optical fiber bundle. The photo-acoustic apparatus 10 comprises a housing 16 having an opening 18. The end 12 of the optical waveguide device 14 extends through the opening 18 into the housing 16. Preferably the housing 16 is hermetically sealed and the opening 18 in the housing 16 is capable of sealably receiving the end 12 of the optical waveguide device 14.

A gas fills the housing 16 and is capable of absorbing energy that exits the end 12 of the optical waveguide device 14. The gas increases in pressure corresponding to the energy absorbed.

The photo-acoustic detector 10 is also comprised of a pressure sensor such as a capacitor microphone 20 which is disposed in the housing 16. The capacitor microphone is capable of sensing the pressure of the gas and producing an electrical signal proportional to the energy which exits the optical waveguide device 14.

Preferably the housing 16 has a first chamber 22 and a second chamber 24. The second chamber 24 communicates with the first chamber 22. The capacitor microphone 20 is preferably disposed in the second chamber 24 and the opening 18 in the housing 16 preferably communicates with the first chamber 22.

The photo-acoustic apparatus 10 preferably also is comprised of a highly reflective shield 26 disposed in the housing 16 between the end 12 of the optical waveguide device 14 and the capacitor microphone 20. The highly reflective shield 26 reduces black body absorption. There is also an amplifier 28 electrically connected to the capacitor microphone 20 for amplifying the signal produced by the capacitor microphone 20.

The photo-acoustic apparatus 10 can also include a light source 30 disposed such that light produced therefrom enters the optical waveguide device 14. An interruptor 32 disposed between the light source 30 and the optical waveguide device 14, can be used to interrupt or chop the light entering the optical waveguide device 14.

The photo-acoustic apparatus 10 can be used to selectively detect energy at a specific wavelength. In one embodiment, the gas filling the housing 16 absorbs energy that exits from the end 12 of the optical waveguide device 14 only at a specific wavelength. In another embodiment of the photo-acoustic apparatus 10 with respect to selective detection, a gas fills the housing 16 which does not absorb energy exited from the end of the optical waveguide device 14. A solid absorber 34 preferably having a hemispherical shape, is disposed in the housing 16 such that it receives the energy which exits the end 12 of the optical waveguide device 14. The solid absorber 34 which absorbs energy at a select wavelength, is heated by the energy. The solid absorber 34 in turn heats the gas causing the pressure of the gas to increase. For example, if the energy to be detected is in the visible or infrared region, argon can be used as the gas which fills the housing 16. The embodiment of the photo-acoustic apparatus 10 having a solid absorber 34 can be used to non-selectively detect the energy exiting from the end 22 of the optical waveguide device 14 if the solid absorber 34 has black body absorption characteristics. Such a solid absorber 34 could be carbon black.

The photo-acoustic apparatus 10 can also have a second optical waveguide device and a second housing, similar to the optical waveguide device and housing described above. The second optical waveguide device extends through the opening in the second housing. The optical waveguide devices 14 are then reference and sensor optical waveguide devices of the photo-acoustic apparatus 10 and can be used as described in U.S. Pat. Nos. 3,180,984 to Fertig et al. and 4,608,344 to Carter et al. The light source 30 and interruptor 32 is common to the sensor and reference optical waveguide devices.

In a preferred embodiment, the photo-acoustic apparatus 10 is used to determine the level of carbon dioxide dissolved in a liquid. The liquid is placed on the surface of the optical waveguide device 14. A portion of the light passing through the optical waveguide device 14 escapes into the liquid, then due to the index of refraction of the liquid, the light that has escaped the optical waveguide device 14 is bent and re-enters the optical waveguide device 14. If there is dissolved carbon dioxide in the liquid, a portion of the light propagating through the optical waveguide device 14 is absorbed in the liquid. The photo-acoustic apparatus 10 is made selective to the detector of carbon dioxide by filling the housing 16 with carbon dioxide gas. Then the energy exiting the end 12 of the optical waveguide device 14 is absorbed by the gas causing a proportional increase in the pressure of the gas. The signal produced by the capacitor microphone 20 is calibrated based on the dissolved carbon dioxide in the liquid.

While the preferred embodiment provides an example of detecting dissolved carbon dioxide in a liquid, the photodetector apparatus 10 can be used to analyze any liquid or solid that selectively absorbs light energy.

What is claimed is:

1. A photo-acoustic apparatus for detecting energy that exits from an end of an optical waveguide device comprising:

a housing having an opening through which the end of the optical waveguide device is inserted into the housing;

a solid absorber disposed in a first chamber of the housing such that it receives the energy which exits the end of the optical waveguide device and is heated corresponding to the energy which exits the end of the optical waveguide;

a gas which fills the housing and which is not capable of absorbing the energy which exits the end of the optical waveguide but which is capable of being heated by the solid absorber such that the pressure of the gas increases;

a capacitor microphone disposed in a second chamber of said housing which is capable of sensing the pressure in the gas and producing an electrical signal proportional to the energy which exits the optical waveguide device; and a highly reflective shield disposed between the first chamber and the second chamber such that it permits gas communication therebetween but reflects light onto the solid absorber and reduces black body absorption by the capacitor microphone.

2. A detector as described in claim 1 wherein the gas is argon.

3. A detector as described in claim 1 wherein the solid absorber is carbon black.

* * * * *